(12) United States Patent
White et al.

(10) Patent No.: US 7,458,615 B2
(45) Date of Patent: Dec. 2, 2008

(54) CONNECTOR

(75) Inventors: Craig Karl White, Auckland (NZ); Jason Peter Van Beurden, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 0 days.

(21) Appl. No.: 10/956,895

(22) Filed: Oct. 1, 2004

(65) Prior Publication Data

US 2005/0077726 A1 Apr. 14, 2005

(30) Foreign Application Priority Data

Oct. 3, 2003 (NZ) .................................. 528683

(51) Int. Cl.
*F16D 27/00* (2006.01)
(52) U.S. Cl. ....................... 285/272; 285/914
(58) Field of Classification Search ......... 285/114–116, 285/272, 148.19, 148.21, 148.2, 148.4, 147.1, 285/304, 914, 913, 921, 417, 276, 315, 316
See application file for complete search history.

(56) References Cited

U.S. PATENT DOCUMENTS

| 626,932 | A | | 6/1899 | Reed et al. |
|---|---|---|---|---|
| 3,881,753 | A | * | 5/1975 | Bochory ....................... 285/82 |
| 3,930,674 | A | | 1/1976 | Jonsson ........................ 285/80 |
| 4,111,514 | A | * | 9/1978 | Brishka et al. ............... 285/914 |
| 4,266,815 | A | * | 5/1981 | Cross ........................... 285/330 |
| 4,281,487 | A | * | 8/1981 | Koller ......................... 52/167.1 |
| 4,619,640 | A | * | 10/1986 | Potolsky et al. ................ 604/7 |
| 4,913,471 | A | | 4/1990 | Huneke |
| 5,051,539 | A | * | 9/1991 | Leathers-Wiessner ...... 174/15.7 |
| 5,116,088 | A | | 5/1992 | Bird |
| 5,179,976 | A | * | 1/1993 | Boland et al. ............... 285/316 |
| 5,330,235 | A | * | 7/1994 | Wagner et al. ................ 285/81 |
| 5,586,791 | A | * | 12/1996 | Kirchner et al. ............. 285/179 |
| 5,725,511 | A | * | 3/1998 | Urrutia ....................... 604/533 |
| 5,803,509 | A | * | 9/1998 | Adams ........................ 285/114 |
| 6,328,349 | B2 | * | 12/2001 | Bandlow et al. ............ 285/319 |
| 6,491,034 | B1 | | 12/2002 | Gunaratnam et al. |
| 6,702,333 | B1 | * | 3/2004 | Oetiker ........................ 285/49 |
| 6,893,055 | B2 | * | 5/2005 | Thomas et al. .............. 285/319 |

FOREIGN PATENT DOCUMENTS

EP 0310369 A1 * 4/1989
EP 0586992 A1 * 3/1994

* cited by examiner

*Primary Examiner*—Aaron M Dunwoody
(74) *Attorney, Agent, or Firm*—Trexler, Bushnell, Giangiorgi, Blackstone & Marr, Ltd.

(57) ABSTRACT

A connector for use with a conduit to supply gases to a user is disclosed. The connector comprises a pair of connectors, adapted to fit together and swivel relative to one another. More particularly, the connector may comprise a female and male connector assemblies, adapted to be push fit together. The female connector assembly preferably has an extended shoulder and a number of triangular guide slots, the slots being shaped so as to be wider at one end. The male connector assembly preferably comprises a connector and a sleeve that when joined, cannot be easily separated by axial or torsional tension applied to either, but may rotate freely relative to each other. The sleeve preferably has a number of guide ridges running axially along its outside surface that slidably mate with the guide slots on the female connector.

9 Claims, 6 Drawing Sheets

CONNECTOR

BACKGROUND OF THE INVENTION

1. Field of the Invention

This invention relates to a connector for gas delivery hoses, and in particular to a connector that allows for a delivery hose to rotate relative to another.

2. Summary of the Prior Art

There are currently a wide variety of swivels available for many applications, from fishing line to high pressure hydraulic lines. Many of the swivels that can be used for fluid conveyance can also be used for gas conveyance. Most of these swivels are sealed, commonly by "O" rings or gaskets, and lock together, either by capture with a threaded part, pinion mechanism or circlip.

In particular, U.S. Pat. No. 626,932 describes two sections of pipe joined by a collar. A shoulder on one pipe (female expanded section) and a pinion on the other (male reducing section) are utilised to enable mating. The female pipe is captured by the collar, the pinion on the other pipe then locks into a "T" shaped groove in the collar, allowing the female pipe to rotate. Captured between the two pipes are two washers. This invention is intended for rigid pipes as a replacement for threaded couplings used in plumbing.

U.S. Pat. No. 4,913,471 is very similar to the above swivel, but this swivel utilises two pinions and two grooves along with different placement of the washers. The intended use for this joint is in the dairy industry, for removing torsion in milking lines.

U.S. Pat. No. 6,491,034 discloses an elbow swivel used for patient gas delivery. It has components that swivel relative to each other and are all mated using a circlip or similar device to capture one part within another. This swivel may not be airtight and the circlip must be removed to break the connection between swivel components. This complicates the attachment and detachment of parts.

SUMMARY OF THE INVENTION

It is an object of the present invention to attempt to provide a connector which goes some way to overcoming the above mentioned disadvantages in the prior art or which will at least provide the industry with a useful choice.

Accordingly in a first aspect the invention consists in a connector for use with a conduit to supply gases to a user comprising:

a pair of connectors, adapted to fit together and swivel relative to one another, and a collar enclosing the connection between said pair of connectors, said collar capable of swivelling relative to each of said pair of connectors.

Preferably said collar includes an aperture capable of receiving a lanyard or the like.

Preferably said collar and said pair of connectors are made from a plastics material.

Preferably said collar includes interference ridges to retain said pair of connectors together.

Preferably said pair of connectors is a male connector or male assembly and a female connector.

Preferably said pair of connectors is a male connector and a female connector.

Preferably said female connector includes a plurality of guide slots for use with said male connector.

Preferably said plurality of guide slots are shaped so as to be wider at one end than they are along the remainder of their length.

Preferably said plurality of guide slots has a cross-sectional profile that is rectangular.

Preferably said male connector includes a sleeve and a male portion, where said sleeve is capable of being attached to said male portion.

Preferably said sleeve is permanently attached to said male portion yet rotates about said male portion and is capable of rotating relative to said collar.

Preferably said sleeve includes a plurality of guide ridges running axially along its outside surface, said plurality of guide ridges corresponding to said guide slots on said female connector, such that upon connection of said male connector and said female connector said plurality of guide ridges slidably mate with said plurality of guide slots on said female connector.

Alternatively said male connector includes a plurality of guide slots and said female connector has a sleeve clipped to it that includes a plurality of guide ridges that mate with said guide slots on said male connector.

BRIEF DESCRIPTION OF THE DRAWINGS

The preferred forms of the present invention will now be described with reference to the accompanying drawings.

DETAILED DESCRIPTION OF THE PREFERRED EMBODIMENTS

Figure 1:
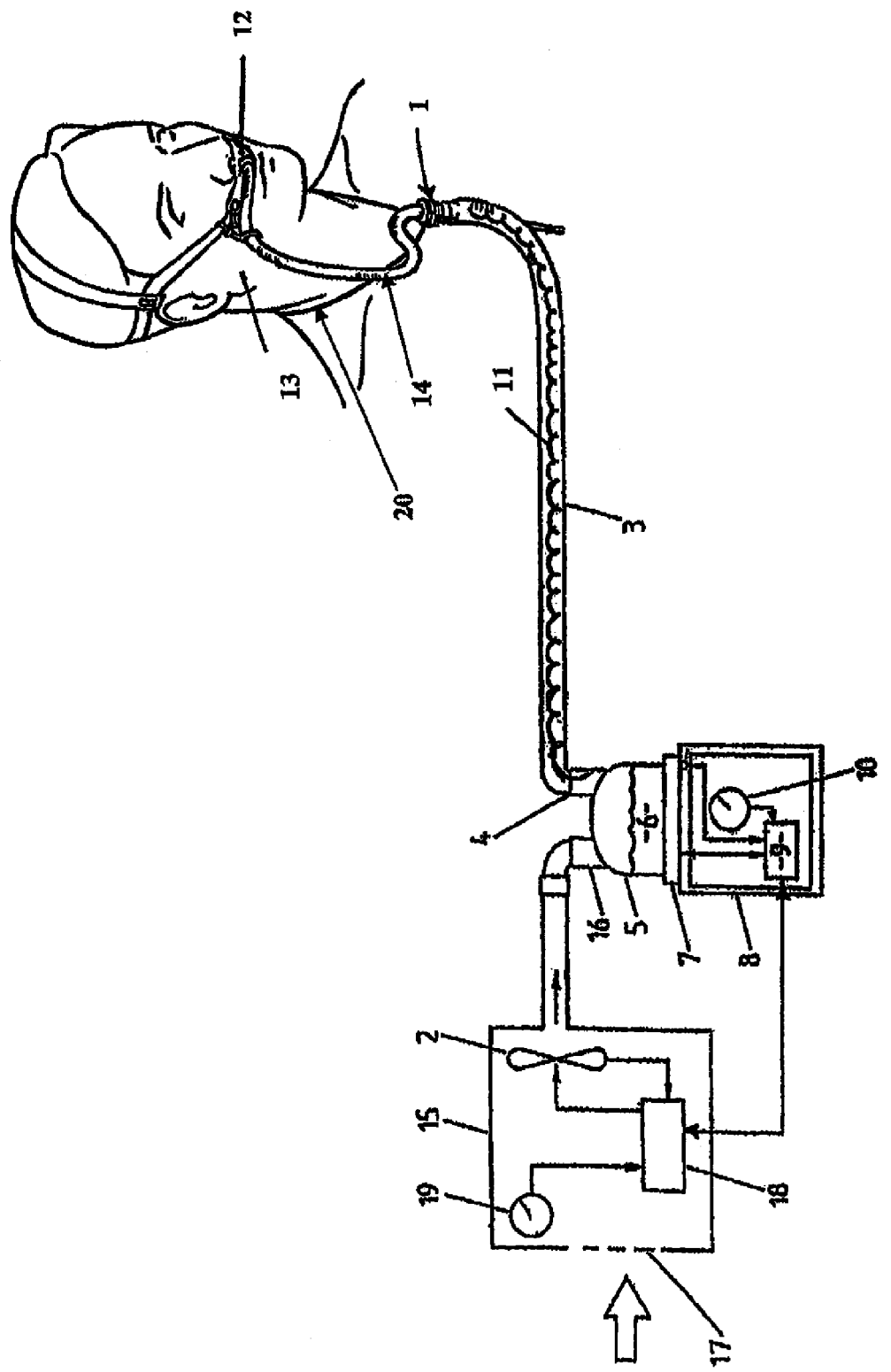
FIG. 1 is a block diagram of a ventilation and humidifying circuit as might be used in conjunction with the connector of the present invention.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Referring to FIG. 1, a ventilation and humidifying circuit as might be used with the connector 1 of the present invention is shown. A patient 13 is receiving humidified and pressurised gases through a nasal cannula 12 connected to a humidified gases transportation pathway or inspiratory conduit 3 that in turn is connected to a humidifier 8 (including humidification chamber 5) supplied with gases from a blower 15 or other appropriate gases supply means. In other forms of the invention gases may be supplied to the patient by alternative patient interfaces, such as a nasal or full-face mask.

The inspiratory conduit 3 is connected to the outlet 4 of the humidification chamber 5 that contains a volume of water 6. Humidification chamber 5 is preferably formed from a plastics material and may have a highly heat conductive base (for example, an aluminium base) which is in direct contact with a heater plate 7 of humidifier 8. The humidifier 8 is provided with control means or electronic controller 9, which may comprise a microprocessor based controller, executing computer software commands stored in associated memory. Gases flowing through the inspiratory conduit 3 are passed to the patient through a connector 1 that connects the inspiratory conduit 3 to the patient end conduit 14 that attaches to the nasal cannula 12.

Controller 9 receives input from sources such as user input means or dial 10 through which a user of the device may, for example, set a predetermined required value (preset value) of humidity or temperature of the gases supplied to patient 13. In response to the user set humidity or temperature value input via dial 10 and other possible inputs such as internal sensors that sense gases flow or temperature, or by parameters calculated in the controller, controller 9 determines when (or to what level) to energise heater plate 7 to heat the water 6 within humidification chamber 5. As the volume of water 6 within humidification chamber 5 is heated, water vapour begins to fill the volume of the chamber above the surface of the water and is passed out of the humidification chamber 5 outlet 4 with the flow of gases (for example air) provided from a gases supply means or blower 15 which enters the humidification chamber 5 through inlet 16. It should be noted that it is possible to obtain the relationship between the humidity of the gases in humidification chamber 5 and the temperature of the heater plate 7. Accordingly, it is possible to utilise the heater plate temperature in an algorithm or a look-up table to determine the humidity of the gases. The blower 15 may be provided with a variable speed pump or fan 2 that draws air or other gases through the blower inlet 17. The speed of the variable speed pump or fan 2 may be controlled by a further control means or electronic controller 18 that responds either to inputs from controller 9 or to user set predetermined required values (preset values) of pressure or fan speed, via dial 19. Alternatively the function of this controller 18 can be combined with the other controller 9.

A heating element 11 may be provided within the inspiratory conduit 3 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heater element effectively replaces the energy lost from the Oases through conduction and convection during transit through the conduit. Thus the conduit heater element ensures the gases delivered are at an optimal temperature and humidity Swivel Connector With reference to FIGS. 1, 2 and 3, the preferred embodiment of the connector of the present invention will now be described.

As shown in FIG. 1, the connector 1 is a swiveling connector and is preferably attached to the patient via a lanyard 20, which sits around the patient's 13 neck. Although the connector 1 may be attached to the patient by other means this arrangement eliminates the necessity of clipping the system to the patients clothing or bedclothes. The connector 1 is preferably comprised of three main components; a collar 21, humidifier end part 23 and a patient end part 22. All of these components are tubular in shape. The lanyard 20 is connected to the swivel connector 1 by way of the collar 21, for example by the loop or aperture 24 formed in the collar 21, and any mechanical load that might arise from carrying the weight of the conduits, or from movement of the patient, is carried by the collar 21. Consequently, little or no load is placed on the conduit 14, or patient interface (in this case, the nasal cannula 12). The inspiratory conduit 3 and patient end conduit 14 are sealably mated to the free ends of the patient end and humidifier end parts 22, 23.

The connector 1 of the present invention allows components in a patient connection system to be connected or disconnected from each other easily, thus enabling easy disconnection and reconnection of the patient interface 12 and gases supply with minimal disturbance to the patient or system.

Figure 2:
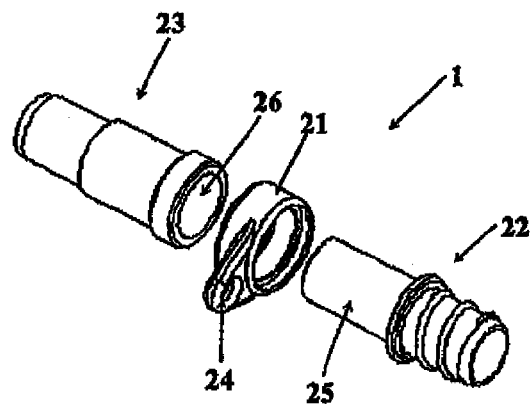
FIG. 2 is an exploded perspective view of the connector of the present invention.
Figure 3:
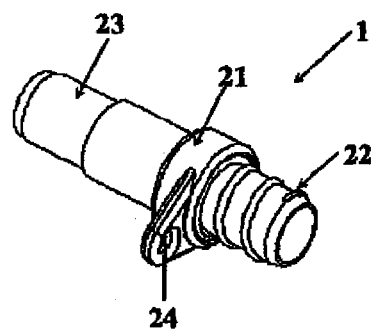
FIG. 3 is a perspective view of the connector of the FIG. 2.

In the preferred embodiment of the connector 1 as shown in FIGS. 2 and 3, the humidifier end connector 23 and patient end connector 22 mate by way of a male/female connection. In the preferred form of the connector of the present invention the humidifier end part 23 is a female connector and the patient end part 22 a male connector. To assemble the connector 1 a male connection portion 25 on the patient end connector 22 passes through the central opening of the collar 21 into the female aperture 26 of the humidifier end part 23 In other forms of the connector 1 of the present invention the humidifier end part 23 may have a male fitting and the patient end part 22 a female fitting.

Figure 4:
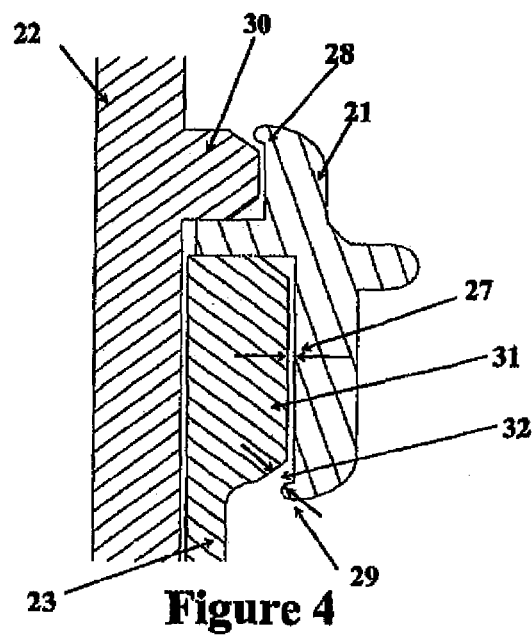
FIG. 4 is a partial cross-section of the connector of FIG. 2 showing the interference connection between the patient end connector, the collar and the humidifier end connector of the present invention.

Referring to FIGS. 3 and 4, when assembled, the patient end connector 22, humidifier end connector 23 and collar 21 freely rotate relative to each other. The clearance distance 27 between the surfaces of the collar 21 and humidifier end part 23 and collar 21 and patient end part 22 is typically 0.1 mm on the radius. As there is free movement between these three components, there is a reduced risk of the components twisting and also a reduced risk of twisting, kinking, or pinching of the air supply hoses (inspiratory conduits 3, 14) from the gases delivery system to the patient interface 12. This has the advantage of ensuring the gas flow will not be inadvertently shut off because a conduit in the system has been pinched shut, and there is also less likelihood of any of these three components becoming damaged through excessive torsion stresses.

Referring to FIG. 4, the patient end part 22 and humidifier end part 23 are held together by a pair of interference protrusions 28, 29 formed on the inner surface of the collar 21. The interference protrusions 28, 29 allow positive capture of the circular interference ridges 30, 31 formed on the patient end part 22 and humidifier end part 23, respectively. On assembly of the connector 1, or on disconnection and reconnection of the patient interface 12 and/or inspiratory conduit 3, the patient end part 22 and humidifier end part 23 are pushed into (on assembly or connection), or pulled out of (on disconnection) collar 21 so that the interference ridge 30 engages with or disengages from the protrusion 28 and the ridge 29 engages with or disengages from the protrusion 31. The interference radius 32 is typically 0.2 mm.

In the preferred embodiment, the interference ridge 31 on the humidifier end part 23 is an extended circular shoulder that provides accurate alignment of the humidifier end part 23 with the collar 21 and prevents loss of capture between the collar 21 and the humidifier end connector 23 when the patient end connector 22 is removed.

The collar 21 does not form a perfect seal with either the humidifier end part 23 or patient end part 22; the connector 1 therefore has a low leak rate. The connector 1 is therefore ideal for low-pressure systems.

Figure 5:
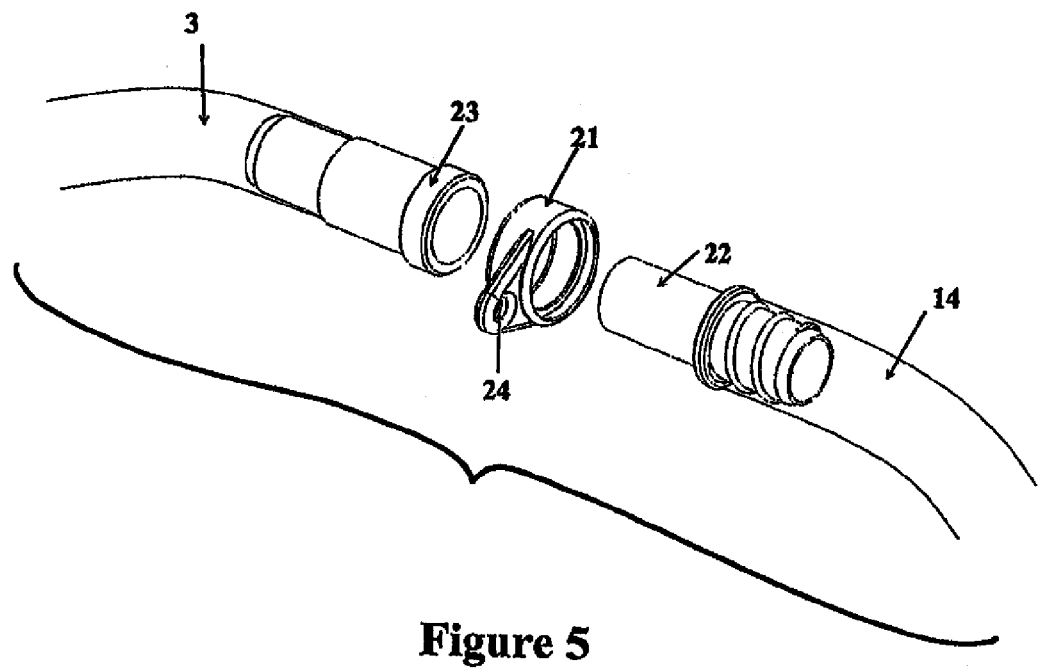
FIG. 5 is an exploded view of the connector of FIG. 2, where the connector is attached to the humidifier side conduit and patient side conduit.

FIG. 5 shows the connector 1 in use with the inspiratory conduit 3 and the patient end conduit 14. The patient end part 22 is mated (by push fit, threading to or other appropriate fastening mechanisms) into the end of the patient end conduit 14. The humidifier end connector 23 is similarly mated to the inspiratory conduit 3.

Alternative Embodiment of the Connector

The connector of the present invention may be provided in an alternative embodiment as shown in FIGS. 6 to 10. This embodiment provides unique mating for user safety. Some systems may become dangerous to the user if inappropriate equipment is attached. There is therefore a need for connecting parts to have unique mating so that only parts with the correct geometry will fit together.

Figure 6:
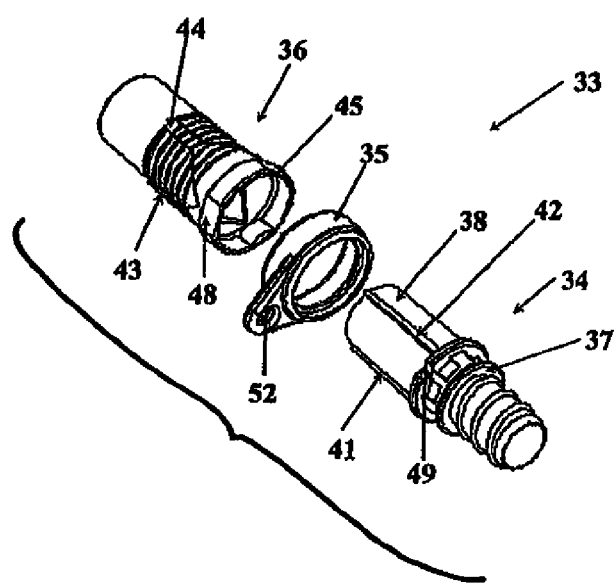
FIG. 6 is an exploded perspective view of the alternative embodiment of the connector of the present invention.

With reference to FIG. 6, the alterative connector 33 is shown. As with the earlier embodiment this connector has a humidifier end part 36, a collar 35 (with aperture 52) and patient end part 34. The patient end part 34 is shown in more detail and exploded in FIG. 7. As shown the patient end part 34 is comprised of two parts, a male portion 37 (similar to the male side connector of the first embodiment) and a ridged tubular sleeve 38. The tubular sleeve 28 is fitted over the male portion 37 of the patient end part 34 and the end 39 of the sleeve 38 makes an interference snap fit with a lip 40 formed on the male portion 37. This connection between the sleeve 38 and lip 40 allows the male portion 37 and sleeve 38 to rotate freely relative to each other. Once made, this connection is permanent (i.e. it is not intended that this connection be undone when the patient interface and gases supply is disconnected and reconnected during normal working operations).

Figure 7:
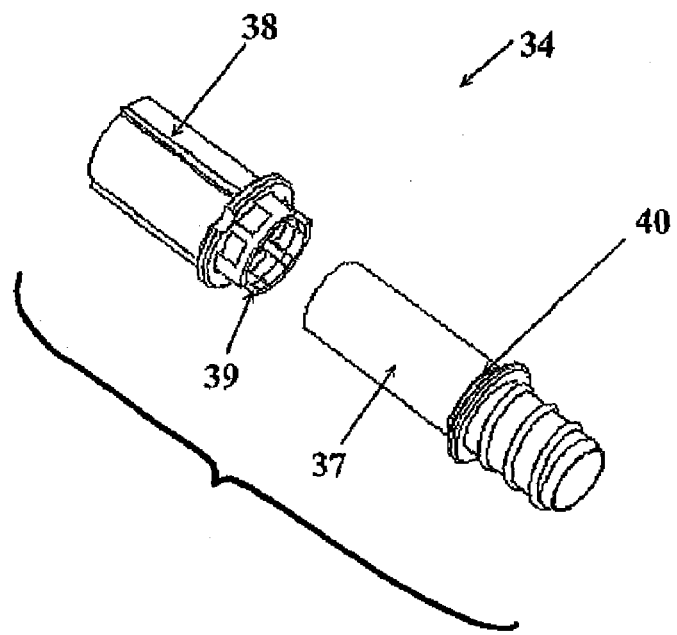
FIG. 7 shows the male portion and sleeve that combine to form the patient end connector assembly used in the alternative embodiment of the connector of the present invention.
Figure 8:
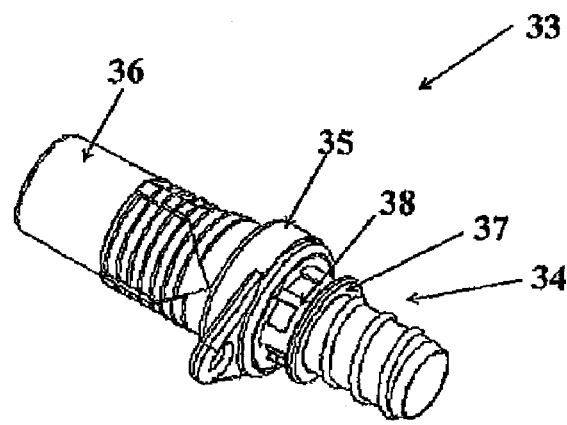
FIG. 8 is a perspective view of an alternative embodiment of the connector of the present invention in an assembled state.

In a similar manner to previously described, and with reference to FIGS. 6 to 8, the patient end part 34, consisting of the male portion 37 and sleeve 38, is mated to the humidifier end part 36. In this alternative embodiment, the sleeve 38 has a number of ridges 41, 42 formed in it. Preferably the sleeve 38 has three ridges spaced equidistant on its circumference, although only two are shown in FIG. 6. These ridges 41, 42 are aligned longitudinally with the axis of the sleeve 38. The ridges 41, 42 correspond to guide slots 43, 44 moulded into the surface of the humidifier end part 36. These guide slots 43, 44 are open at the end 45 of the humidifier end part 36, such that when the patient end part 34 is assembled with it, the ridges are aligned into the slots 43, 44 the parts 34, 36 are slid together, The parts 34, 36 are therefore mated in a non-rotating manner. This mating arrangement is shown in cross-section in FIG. 9. At the end 45, the guide slots 43, 44 may be wider as shown in FIGS. 6 and 8 in order to facilitate alignment and mating between the two parts 34, 36.

Figure 9:
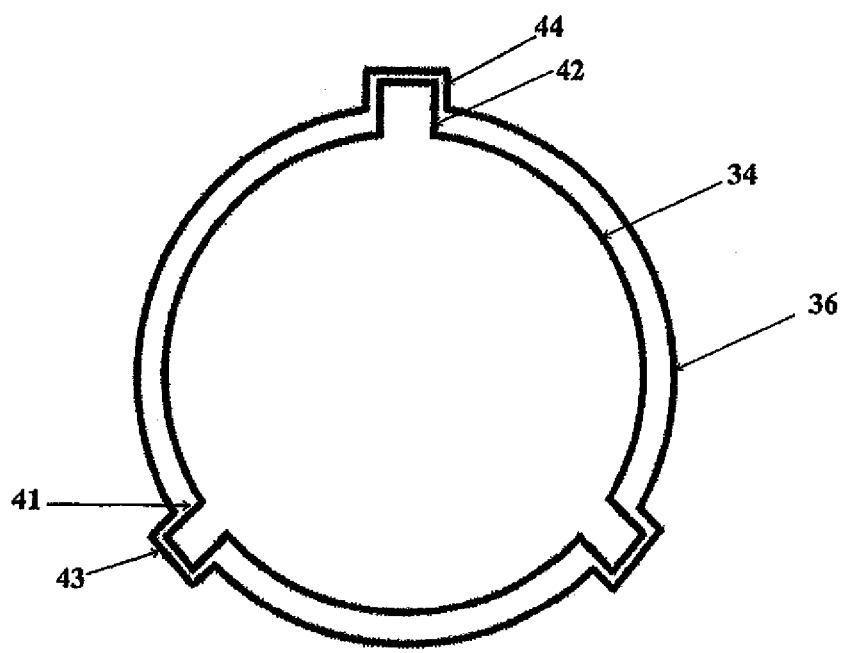
FIG. 9 shows the mating arrangement of an alternative embodiment in cross-section.
Figure 10:
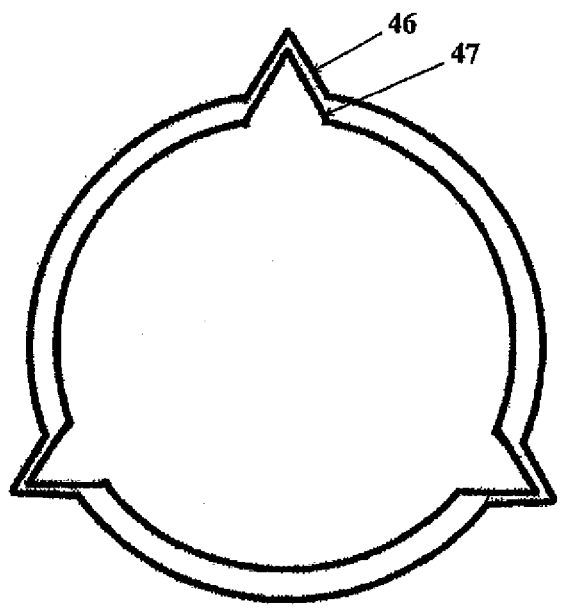
FIG. 10 is a cross-section of a further mating arrangement of the alternative embodiment.

This ridge and slot arrangement is intended to prevent insertion of mismatched connectors, which may lead to dangerous operation of equipment. The cross-sectional profile of the ridges and slots, or the number of matched ridges and slots, can therefore be varied, and the user can choose different profiles for different applications. One possible alternative profile is shown in cross-section in FIG. 10. Here, the ridges 46 and slots 47 may be triangular in profile not trapezoidal as shown in FIG. 9.

In the alternative embodiment, the connection between the patient end part 34 and humidifier end part 36 is similar to that described above in relation to FIG. 4, that is, with an interference fit between the collar 35 and the parts 34, 36.

Alternatively, the sleeve 38 and the humidifier end part 36 may clip together directly. Here the collar 35 is still present, allowing attachment of the lanyard 20, and enabling the transfer of the mechanical load to the collar 35 as before.

Again, the collar 35 can rotate freely relative to the connectors 34, 36. Thus this alternative embodiment of the connector 33 retains the advantages of ensuring the gas flow will not be inadvertently shut off, and a reduced likelihood of component damage.

Furthermore, to prevent mating of inappropriate connectors about either the humidifier end part 36 or patient end part 34, these parts are moulded such that they would leak if a foreign part was connected to them. For example, in FIG. 6, the end 45 of the humidifier end part 36 is moulded such that the circumference is not completely circular but is provided with at least one flat side (for example see flat side 48 on FIG. 6) about the circumference of the end 45. Similarly, at least one cut out 49 may be provided on the patient end part 34. Therefore, in the event that a foreign circular connector is attached to either the humidifier end part 36 or patient end part 34 the flat side(s) 48 or cut out(s) 49 will cause a leak to occur between the foreign connector and part 34, 36.

Figure 11:
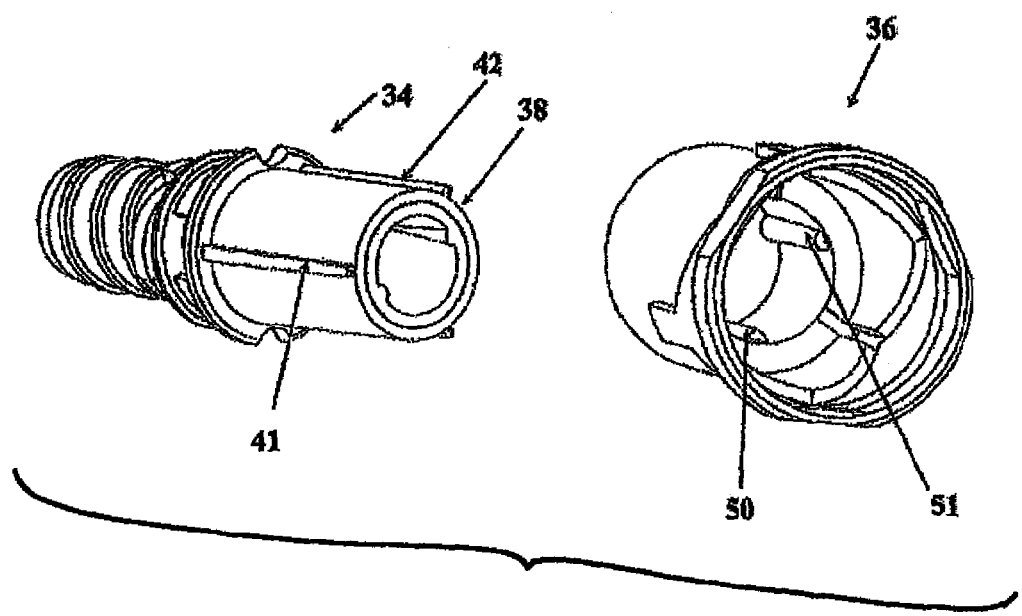
FIG. 11 is an alternative exploded perspective view of the humidifier end part and patient end part of FIG. 6.

Similarly, axial ridges may be provided on internal non-mating surfaces of the humidifier end part 36 and/or patient end part 34. For example, in FIG. 11 the humidifier end part 36 is shown having internal axial ridges 50, 51. Ridges such as these will provide leak paths and cause poor mating if inappropriate connectors are forced into either the humidifier end part 36 or patient end part 34.

We claim:

1. A connector for use with a conduit to supply gases to a user comprising:

male connector and a female connector adapted to fit together to form a pneumatic connection in use, said male connector including a sleeve fitted over and permanently connected to at least part of said male connector in such a manner that said sleeve can freely rotate relative to said male connector, said sleeve adapted to mate with said female portion in use, one of said connectors adapted for attachment to one end of said conduit, a collar which in use encloses said pneumatic connection that in use is made between said male connector and said female connector, said collar and said male and female connectors sized relative to one another so that in use said collar can freely swivel relative to each of said connector parts, said collar including interference protrusions adapted to retain said of male connector and said female connectors together, said interference protrusions and said male and female connectors further sized relative to one another so that said collar and said male and female connectors can be connected or disconnected from each other easily by a user, and wherein one of said male or said female connectors includes a plurality of guide slots, and the other of said connectors includes a plurality of complimentary guide ridges, said slots receiving said ridges in use, and said slots and ridges shaped so that a pair of mismatched connector parts cannot be connected.

2. A connector as claimed in claim 1 wherein said female connector includes said plurality of guide slots and said sleeve includes said plurality of guide ridges that mate with said guide slots.

3. A connector as claimed in claim 2 wherein said plurality of guide slots are shaped so as to be wider at one end than they are along the remainder of their length.

4. A connector as claimed in claim 3 wherein said guide ridges run axially along the outside surface of said sleeve and correspond with said guide slots on said female connector, such that upon connection of said male connector and said female connector said plurality of guide ridges slidably mate with said plurality of guide slots.

5. A connector as claimed in claim 4 wherein said plurality of guide slots are shaped so as to be wider at one end than they are along the remainder of their length.

6. A connector as claimed in claim 5 wherein each of said plurality of guide slots has a cross-sectional profile that is rectangular.

7. A connector as claimed in claim 5 wherein each of said plurality of guide slots has a cross-sectional profile that is triangular.

8. A connector as claimed in claim 6 or 7 wherein said collar includes an aperture capable of receiving a lanyard.

9. A connector as claimed in claim 6 or claim 7 wherein said collar and said pair of connectors are made from a plastics material.

* * * * *